US006545008B1

(12) United States Patent
Lee et al.

(10) Patent No.: US 6,545,008 B1
(45) Date of Patent: Apr. 8, 2003

(54) PYRIMIDINE DERIVATIVES AND PROCESSES FOR THE PREPARATION THEREOF

(75) Inventors: Jong Wook Lee, Kyonggi-do (KR); Bong Yong Lee, Kyonggi-do (KR); Chang Seop Kim, Kyonggi-do (KR); Seung Kyu Lee, Kyonggi-do (KR); Song Jin Lee, Kyonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 09/856,048

(22) PCT Filed: Nov. 9, 1999

(86) PCT No.: PCT/KR99/00669
§ 371 (c)(1),
(2), (4) Date: May 17, 2001

(87) PCT Pub. No.: WO00/29403
PCT Pub. Date: May 25, 2000

(30) Foreign Application Priority Data

Nov. 17, 1998 (KR) ............................................ 98-49164

(51) Int. Cl.$^7$ ........................ C07D 401/04; A61K 31/444
(52) U.S. Cl. ........................ 514/275; 514/256; 544/328; 544/324
(58) Field of Search .................. 544/328, 324; 514/275, 256

(56) References Cited

U.S. PATENT DOCUMENTS

| | | | |
|---|---|---|---|
| 3,956,495 A | 5/1976 | Lacefield | 424/251 |
| 3,960,861 A | 6/1976 | Danilewicz et al. | 424/251 |
| 3,980,781 A | 9/1976 | Snell et al. | 424/251 |
| 4,000,138 A | 12/1976 | Snell et al. | 424/251 |
| 4,044,136 A | 8/1977 | Danilewicz et al. | 424/251 |
| 5,064,833 A | 11/1991 | Ife et al. | 514/260 |
| 5,075,316 A | 12/1991 | Hubele | 514/275 |
| 5,276,186 A | 1/1994 | Waditschatka | 564/238 |
| 5,525,604 A | 6/1996 | Lee et al. | 514/256 |

FOREIGN PATENT DOCUMENTS

| | | |
|---|---|---|
| EP | 0 230 871 A2 | 8/1987 |
| EP | 0 337 943 A2 | 10/1989 |
| EP | 0 376 806 A2 | 8/1990 |
| EP | 0 388 838 A2 | 9/1990 |
| EP | 0 560 726 A2 | 9/1993 |
| EP | 0 640 599 A1 | 3/1995 |
| GB | 1182584 | 2/1970 |
| WO | 91/18887 | 12/1991 |
| WO | 92/07844 | 5/1992 |
| WO | 92/18498 | 10/1992 |
| WO | 94/14795 | 7/1994 |
| WO | 95/10506 | 4/1995 |
| WO | 96/05177 | 2/1996 |
| WO | 97/42186 | 11/1997 |
| WO | 98/18784 | 5/1998 |
| WO | 98/43968 | 10/1998 |

OTHER PUBLICATIONS

Chemical Abstracts, "Preparation of substituted pyrimide derivatives as analgesics and antiinflammatory agents", vol. 122, Abstracts No. 290883s, p. 1041, col. 1, Jun. 5, 1995.

Chemical Abstracts, "Pyrimidine derivative for treatment of uncerative colitis", vol. 120, Abstracts No. 86447g, p. 654, col. 2, Feb. 21, 1994.

Chemical Abstract, "Oral preparations containing anti-allergy pyrimidine derivative", vol. 112, Abstracts No. 87674z, p. 457, col. 1, Mar. 8, 1993.

Chemical Abstracts, "Herbicides. I. 2–(4–Nitroanilino)pyrimidines", vol. 96, Abstracts No. 122741v, p. 697, col. 1, Apr. 12, 1982.

Chemical Abstracts, "Biosynthesis of 1–methyl–1,2,3,4–tetrahdroisoquinoline (1MeTIQ), a possible anti–Parkinsonism agent", vol. 118, Abstracts No. 249869w, p. 347, col. 2, Jun. 21, 1993.

Chemical Abstracts, "Carbon dioxide: a reagent for the protection of nucleophilic centers and the simultaneous activation of electrophilic attack. Part II", vol. 106, Abstracts No. 32801k, p. 526, col. 1, Feb. 2, 1987.

Chemical Abstracts, "Synthesis of dihydroisoquinolines and 1–substituted tetrahydroisoquinolines", vol. 96, Abstracts No. 217665n, p. 726, col. 1, Jun. 21, 1982.

Chemical Abstracts, "An evaluation of the ortho effect in iso–cytosine derivatives: 2–aralkylamino– and 2–arylamino–3,4–dihydropyrimidin–4(3)–ones", vol. 121, Abstracts No. 256215v, p. 1218, col. 2, Nov. 21, 1994.

Chemical Abstracts, "interaction of GTP derivatives with cellular and oncogenic ras–p21 proteins", vol. 114, Abstracts No. 185899p, p. 833, col. 1, May 13, 1991.

Chemical Abstracts, "Alkylation of isoquinoline skeleton in the 1–position. Lithiated 2–pivaloyl– and 2–bis(dimethylamino) phosphinolyl–1,2,3,4–tetrahydroisoquinolines", vol. 99, Abstracts No. 158207b, pp. 597–598, col. 2, Nov. 7, 1983.

Kye Han, et al, "Pharmacokinetics of a New Reversible Proton Pump Inhibitor, YH1885, after Intravenous and Oral Administrations to Rats and Dogs: Hepatic First–pass Effect in Rats", Biopharmaceutics & Drug Disposition, 19(8), pp. 493–500, 1988.

Byung–Nak Ahn et al, "Pharmacokinetic Study of YH1885 (I): Absorption, Distribution and Excretion of $^{14}$C–YH1885 in Rats", Yakhak Hoeji, vol. 41, No. 3, pp. 335–344, 1997.

Kye Han, et al, "Blood Partition Binding of a New Reversible Proton Pump Inhibitor, YH1885", Biopharmaceutics & Drug Disposition, 19(6), pp. 413–415, 1998.

Hyeyoung Kim et al, "Inhibitory Effects of Reversible Proton Pump Inhibitors YH 1238 and YH1885 on Acid Secretion in Isolated Gastric Cells", Korean J. Physiol. Pharmacol., 1(3), pages 337–343, 1997.

Kye Soo Han, et al, "Determination of a new proton pump inhibitor, YH1885, in human plasma and urine by high–performance liquid chromatography", Journal of Chromatography B, 696(2), pp. 312–316, 1997.

*Primary Examiner*—John M. Ford
(74) *Attorney, Agent, or Firm*—Burns, Doane, Swecker & Mathis, LLP

(57) ABSTRACT

The present invention relates to novel pyrimidine derivatives and pharmaceutically acceptable non-toxic salts thereof which possess an excellent inhibitory activity against gastric acid secretion, a pharmaceutical composition containing the same as an active ingredient, and a process for the preparation thereof.

13 Claims, No Drawings

PYRIMIDINE DERIVATIVES AND PROCESSES FOR THE PREPARATION THEREOF

This 371 is a 371 of PCT/KR99/00669, filed Nov. 9, 1999.

FIELD OF THE INVENTION

The present invention relates to novel pyrimidine derivatives and pharmaceutically acceptable non-toxic salts thereof which possess an excellent inhibitory activity against gastric acid secretion, a pharmaceutical composition containing the same as an active ingredient, and a process for the preparation thereof.

BACKGROUND OF THE INVENTION

For the treatment of peptic ulcer disease, various drugs such as antacid, anticholinergic agents, H2-receptor antagonist and proton pump inhibitor have been used. The advent of proton pump inhibitors has rekindled research activities in this field.

However, it has been pointed out that the irreversible mode of action by proton pump inhibitors may induce undesirable effects. Accordingly, various attempts to develop a reversible proton pump inhibitor (i.e., reversible acid pump antagonist) are being actively made. For example, European Patent Nos. 322,133 and 404,322 disclose quinazoline derivatives, European Patent No. 259,174 describes quinoline derivatives, and WO 91/18887 offers pyrimidine derivatives, as reversible proton pump inhibitors.

Further, the present inventors have also reported quinazoline derivatives in WO 94/14795 and pyrimidine derivatives in WO 96/05177 and WO 98/43968.

SUMMARY OF THE INVENTION

The present inventors have carried out further research to develop reversible acid pump antagonists with improved efficacy; and, as a result, have discovered that pyrimidine derivatives having one or more halogen groups at the 5- or 6-position of a pyrimidine nucleus or at the tetrahydroisoquinoline group of the 4-position of the pyrimidine nucleus exhibit excellent acid pump inhibition effects and inhibitory activity against gastric acid secretion.

Accordingly, it is a primary object of the present invention to provide novel pyrimidine derivatives having one or more halogen groups at the 5- or 6-position of a pyrimidine nucleus or at the tetrahydroisoquinoline group of the 4position of the pyrimidine nucleus, and pharmaceutically acceptable non-toxic salts thereof.

It is another object of the present invention to provide processes for preparing said compounds.

It is a further object of the present invention to provide pharmaceutical compositions for treating gastrointestinal diseases containing the same as an active ingredient.

DETAILED DESCRIPTION OF THE INVENTION

In accordance with one aspect of the present invention, there are provided novel pyrimidine derivatives of formula (I) or pharmaceutically acceptable non-toxic salts thereof:

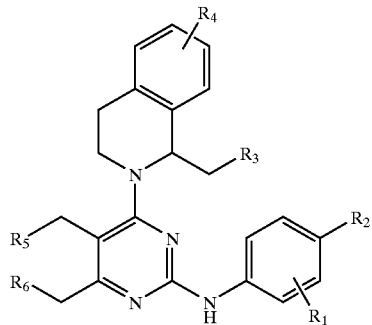

(I)

wherein $R_1$ is hydrogen, methyl, or halogen and $R_2$, $R_3$, $R_4$, $R_5$ and $R_6$ are, independently each other, hydrogen or halogen, provided that when all of $R_3$, $R_4$, $R_5$ and $R_6$ are hydrogen, $R^1$ and $R^2$ are, independently each other, halogen.

Among the pyrimidine derivatives of the present invention, preferred are those wherein $R_1$, $R_2$, $R_3$, $R_4$, $R_5$ and R6 are independently fluoro or chloro.

The present invention also includes, within its scope, pharmaceutically acceptable non-toxic salts of the compounds of formula (I). The non-toxic salts, within the scope of the present invention, may include inorganic or organic salts, such as hydrochloride, maleate, sulfate, phosphate, mesylate, nitrate, tartrate, fumarate, citrate, acetate. In addition, conventional acidic salt forms used in the field of anti-ulcer agents may be included. Such salts may be prepared in accordance with any of the conventional methods.

The present invention further includes, within its scope, processes for the preparation of the compounds of formula (I-1) and (I-2). The compounds of the formula (I-1) and (I-2) may be prepared in accordance with the following methods.

Method for preparation of formula (I-1)

The compound of formula (I-1) may be prepared by halogenating the corresponding hydroxy group of a compound of formula (II) in accordance with Scheme 1 described below.

Scheme 1

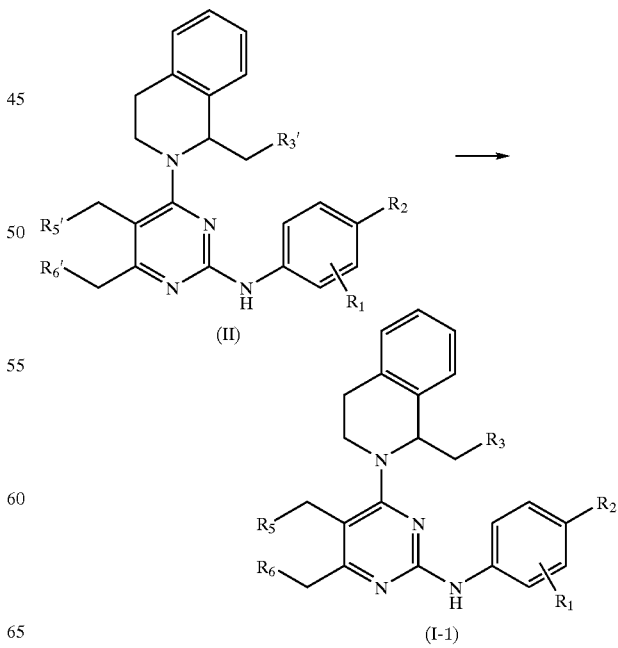

wherein $R_1$ is hydrogen, methyl, or halogen and $R_2$, $R_3$, $R_5$ and R6 are, independently each other, hydrogen or halogen, provided that one or more of $R_3$, $R_5$ and $R_6$ is/are halogen; and $R_3$, $R_5$ and $R_6$ is independently hydrogen or hydroxy, provided that one or more of $R_3$, $R_5$ and $R_6$ are hydroxy.

In the process of Scheme 1, when halogen is fluoro, the compound of formula (I-1) may be prepared by adding (diethylamino)sulfur trifluoride to the solution of the compound of formula (II) in an appropriate solvent. Suitable solvents for this reaction may include chloroform and dichloromethane. The reaction temperature preferably ranges from −78° C. to 25° C. and the reaction time preferably ranges from 4 to 18 hours.

In the process of Scheme 1, when halogen is chloro, the compound of formula (I-1) may be prepared by adding thionyl chloride to the solution of the compound of formula (II) in an appropriate solvent.

The compound of formula (II) may be prepared in accordance with conventional methods (e.g., WO 98/43968).

Method for preparation of formula (I-2)

The compound of formula (I1) which $R_3$, $R_5$ and $R_6$ are hydrogen may be prepared by reacting a compound of formula (III) with a compound of formula (IV) in accordance with Scheme 2 described below.

Scheme 2

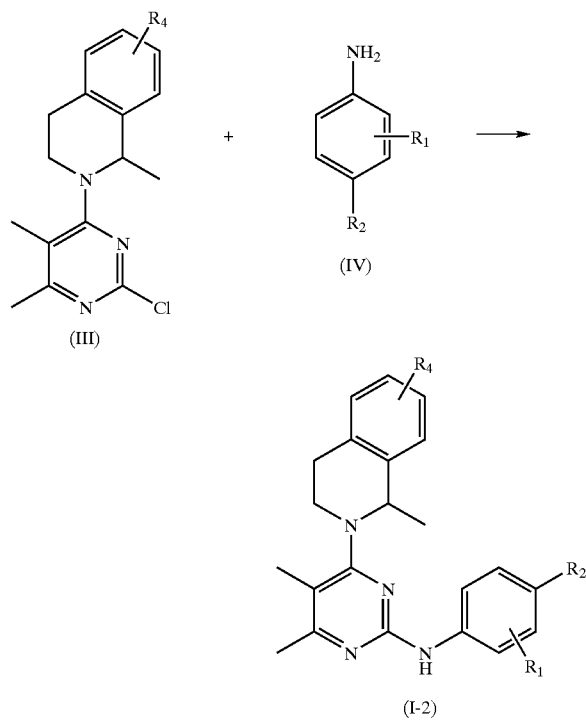

wherein $R_1$ is hydrogen, methyl, or halogen and $R_2$ and $R_4$ are, independently each other, hydrogen or halogen, provided that when $R_4$ is hydrogen, $R_1$ and $R_2$ are, independently each other, halogen.

Suitable solvents for this reaction include dimethylformamide 1,4-dioxane, dimethyl sulfoxide, and propylene glycol. The reaction temperature preferably ranges from 80° C. to 140° C. and the reaction time preferably ranges from 2 to 5 hours.

The compounds of formula (III) may be prepared in accordance with the same method as described in WO 96/05177. And also, tetrahydroisoquinolines substituted with fluoro or chloro group at 5-, 6-, or 7-position of tetrahydroisoquinoline, which are useful as an intermediate for preparing the compound of formula (III), may be prepared in accordance with a known method (e.g., J. Org. Chem., 1991.56, 6034).

The present invention further includes, within its scope, pharmaceutical compositions for treating gastrointestinal diseases, which comprise a therapeutically effective amount of the pyrimidine derivative of formula (I) or a pharmaceutically acceptable non-toxic salt thereof as an active ingredient, and a pharmaceutically acceptable carrier, excipient and/or other additives, if necessary. The active ingredient present in the composition may range from 0.1% to 99.9% by weight thereof.

The pharmaceutical composition of the present invention may be formulated in accordance with conventional methods. For example, the pharmaceutical composition may be formulated into various forms such as solution, suspension or emulsion in an oily or aqueous vehicle, which may contain conventional additives such as a dispersant, suspending agent, or emulsifiers, stabilizer and the like. Alternatively, the active ingredient may be formed into a dried powder that may be dissolved in sterile pyrogen-free water before use.

The compounds of the present invention may be administered, either orally or intraperitoneally, in an amount ranging from 0.1 to 500 mg/kg per day, preferably from 1.0 to 100 mg/kg per day, to human beings or animals suffering from gastrointestinal diseases, depending on the age and body weight of the patient, the nature and severity of the illness and so on. The compounds of the present invention may be formulated for administration in unit dose or multi-dose containers.

The following Examples and Test Examples are given for the purpose of illustration only, and are not intended to limit the scope of the invention.

Preparation 1: Preparation of 1-methyl- 1,2,3,4-tetrahydroisoquinoline

Step 1: N-(2-phenylethyl)acetamide

After phenethylamine (37.8 ml, 0.3mol) and triethylamine (42 ml, 0.3mol) were dissolved in dichloromethane (200 ml), acetyl chloride (20.7 ml, 0.3mol) was dropwise added thereto, while maintaining the reaction temperature below 0° C. The resulting solution was stirred for 10 minutes at room temperature, washed with water dried over anhydrous magnesium sulfate, and concentrated in vacuo to give 45.8 g of the titled compound as a white solid.

Step 2: 1-methyl-3,4-dihydroisoquinoline

The compound (25.3 g, 154.8 mmol) prepared in Step 1 above was added to polyphosphoric acid (250 g) and then stirred for 1.5 hours at 160° C. The reaction mixture was poured into ice water, neutralized with ammonia solution, and extracted with ethyl acetate. The extract was dried over anhydrous magnesium sulfate and concentrated in vacuo. The resulting residue was subjected to silica gel column chromatography (eluent: methanol/dichloromethane =1/20) to give 21.8 g of the titled compound as an oily substance.

Step 3: 1-methyl-1,2,3,4-tetrahydroisoquinoline

To the suspension of sodium borohydride (5.28 g, 138 mmol) in ethanol, was added the compound (19.8 g, 133.8 mmol) prepared in Step 2 above. The reaction mixture was stirred for 1 hour at room temperature, cooled to below 5° C. acidified with diluted hydrochloric acid, neutralized with sodium hydroxide solution, and extracted with ethyl acetate. The ethyl acetate layer was dried over anhydrous sodium sulfate and concentrated in vacuo to give 18.5 g of the titled compound.

Preparation 2: Preparation of 1-methyl-7-fluoro-1,2,
3,4-tetrahydroisoquinoline

Step 1: 6,10b-dihydro-10b-methyl-5H-oxazolo[2,3-a]
isoquinolin-2,3-dione

To the solution of N-[2-(4-fluorophenylethyl)acetamide (5.8 g, 32 mmol) prepared in accordance with the same procedure as in Step 1 of Preparation 1 in dichloromethane (15 ml), oxalyl chloride (3.07 ml, 1.1 eq.) was dropwise added. The reaction mixture was stirred for 30 minutes at room temperature and cooled to below –10 ° C. Aluminum chloride (5.1 g, 1.2 eq.) was added to the reaction mixture and then it was stirred for 18 hours at room temperature. 1N hydrochloric acid solution was added to the reaction mixture, which was then stirred for 1 hour at room temperature. The organic layer was washed with brine and concentrated in vacuo to give 5.2 g of the titled compound.

Step 2: 1-methyl-7-fluoro-3,4-dihydroisoquinoline

To 6,10dihydro-10b-methyl-5H-oxazolo[2,3-a]isoquinolin-2,3-dione (5.2 g) prepared in Step 1 above, methanol (30 ml) and sulfuric acid (1.6 ml) were added. The reaction mixture was refluxed for 18 hours, cooled to room temperature, and concentrated in vacuo. To the resulting residue, 1N hydrochloric acid and dichloromethane were added. The water layer was adjusted to pH 12 with potassium hydroxide solution and extracted with dichloromethane. The extract was washed with water, dried over sodium sulfate, and concentrated in vacuo to give 2.4 g of the titled compound.

Step 3: 1-methyl-7-fluoro-1,2,3,4-tetrahydroisoquinoline

To the solution of 1-methyl-7-fluoro-3,4-dihydroisoquinoline (2.4 g, 14.7 mmol) prepared in Step 2 in methanol (10 ml), sodium borohydride (0.28 g, 1 eq.) was portionwise added. The reaction mixture was stirred for 3 hours and 1N hydrochloric acid solution (20 ml) was added thereto. The reaction mixture was washed with dichloromethane. The water layer was adjusted to pH 12 with potassium hydroxide solution and extracted with dichloromethane. The extract was washed with water, dried over anhydrous sodium sulfate, and concentrated in vacuo to give 2.0 g of the titled compound.

Preparation 3: Preparation of 1-methyl-6-fluoro-1,2,
3,4-tetrahydroisoquinoline

The same procedures as in Preparation 2 above were repeated using N-[2-(3-fluorophenyl)ethyl]acetamide (13.7 g, 75.5 mmol) prepared in accordance with the same procedure as in Step 1 of Preparation 1 as a starting material to afford 6.95 g of the titled compound.

Preparation 4: Preparation of 1-methyl-5-fluoro-1,2,
3,4-tetrahydroisoquinoline

The same procedures as in Preparation 2 above were repeated using N-[2-(2-fluorophenyl)ethyl]acetamide (4.36 g, 24.06 mmol) prepared in accordance with the same procedure as in Step 1 of Preparation 1 as a starting material to afford 1.2 g of the titled compound.

Preparation 5: Preparation of 1-methyl-7-chloro-1,2,
3,4-tetrahydroisoquinoline

The same procedures as in Preparation 2 above were repeated using N-[2-(4-chlorophenyl)ethyl]acetamide (3.8 g, 19.2 mmol) prepared in accordance with the same procedure as in Step 1 of Preparation 1 as a starting material to afford 1.5 g of the titled compound.

Preparation 6: Preparation of 1-methyl-6chloro-2,3,
4-tetrahydroisoquinoline

The same procedures as in Preparation 2 above were repeated using N-(2-(3-chlorophenyl)ethyl]acetamide (12.55 g, 63.5 mmol) prepared in accordance with the same procedure as in Step 1 of Preparation 1 as a starting material to afford 4.56 g of the titled compound.

Preparation 7: Preparation of 1-methyl-5-chloro-1,2,
3,4-tetrahydroisoquinoline

The same procedures as in Preparation 2 above were repeated using N-[2-(2-chlorophenyl)ethyl]acetamide (12.55 g, 63.5 mmol) prepared in accordance with the same procedure as in Step 1 of Preparation 1 as a starting material to afford 5.8 g of the titled compound.

Example 1: Preparation of 5,6-dimethyl-2-(3,4-
difluorophenylamino)-4-(1-methyl-1,2,3,4-
tetrahydroisoquinolin-2-yl)pyrimidine hydrochloride To the solution of 5,6-dimethyl-2-chloro4-(1-methyl-1,2,3,4-tetrahydroisoquinolin-2-yl)pyrimidine (0.5 g, 1.74 mmol) prepared in accordance with WO 96/05177 in propylene glycol (2 ml), were added triethylamine (0.3 ml, 2.09 mmol) and 3,4-difluoroaniline (0.2 ml, 2.09 mmol). The reaction mixture was heated to 140° C., stirred for 18 hours, and cooled to room temperature. The resulting solution was diluted with dichloromethane, washed with water, and dried over anhydrous sodium sulfate. The organic layer was concentrated in vacuo. The resulting residue was subjected to silica gel column chromatography (eluent: ethyl acetate/hexane =⅓), and then treated with ethyl ether solution saturated with hydrochloric acid to afford 0.1 g (13.8%) of the titled compound.

NMR(CDCl$_3$): δ 1.6 (d, 3 H), 2.2 (s, 3 H), 2.4 (s, 3 H), 2.9 (m, 1 H), 3.2 (m, 1 H), 3.6 (m, 1 H), 4.2 (m, 1 H), 5.4 (q 1 H), 7.1 (m, 6 H), 7.8 (m, 1 H), 10.5 (s, 1 H), 14.0 (s, 1 H).

Example 2: Preparation of 5,6-dimethyl-2-(2,4-
difluorophenylamino)-4-(1-methyl-1,2,3,4-
tetrahydroisoquinolin-2-yl)pyrimidine hydrochloride To the solution of 5,6-dimethyl-2-chloro4-(1-methyl-1,2,3,4-tetrahydroisoquinolin-2-yl)pyrimidine (0.8 g, 2.78 mmol) in dimethyl sulfoxide (1.5 ml), was added 2,4-difluoroaniline (0.5 ml, 4.9 mmol). The reaction mixture was heated to 120° C., stirred for 2 hours, and cooled to room temperature. The resulting solution was diluted with ethyl acetate, washed with water and sodium hydroxide solution, and dried over anhydrous magnesium sulfate. The organic layer was concentrated in vacuo. The resulting residue was subjected to silica gel column chromatography (eluent: ethyl acetate/dichloromethane =⅕), and then treated with ethyl ether solution saturated with hydrochloric acid to afford 0.2 g (17%) of the titled compound.

NMR(CDCl$_3$): δ 1.6 (d, 3 H), 2.2 (s, 3 H), 2.6 (s, 3 H), 2.8 (m, 1 H), 3.1 (m, 1 H), 3.5 (m, 1 H), 4.2 (m, 1 H), 5.3 (q, 1 H,), 6.9–7.2 (m, 6 H), 7.8 (q, 1 H), 9.7 (s, 1 H), 14.4 (bs, 1 H).

Example 3: Preparation of 5,6-dimethyl-2-(4-
fluorophenylamino)-4-(1-methyl-7-fluoro-1,2,3,4-
tetrahydroisoquinolin-2-yl)pyrimidine hydrochloride Step 1: 5,6-dimethyl-2-chloro-4-(1-methyl-7-fluoro-1,2,3,4-tetrahydroisoquinolin-2-yl)pyrimidine To the solution of the compound (1.6 g, 9.7 mmol) prepared in Preparation 2 in dimethylformamide (5 ml), were added 5,6-dimethyl-2,4-dichloropyrimidine (1.71 g, 9.7 mmol) prepared in accordance with WO 96/05177 and triethylamine (1.62 ml). The reaction mixture was stirred for 5 hours at 70° C., cooled to room temperature, and diluted with dichloromethane. The resulting mixture was washed with water, dried over anhydrous sodium sulfate, and concentrated in vacuo. The resulting residue was subjected to silica gel column chromatography (eluent:ethyl acetate/hexane =1/5) to give 1.2 g, (40.2%) of the titled compound.

Step 2: 5,6-dimethyl-2-(4-fluorophenylamino)-4-(1-methyl-7-fluoro-1,2,3,4-tetrahydroisoquinolin-2-yl)pyrimidine hydrochloride To the solution of the compound (0.1 g, 0.3 mmol) prepared in Step 1 above in dimethylformamide (5 ml), was added 4-fluoroaniline (0.08 ml, 0.84 mmol). The reaction mixture was refluxed for 3 hours, cooled to room temperature, diluted with dichloromethane, and washed with water. The extracted dichloromethane layer was adjusted to basic with sodium hydroxide solution, washed with water, dehydrated, and concentrated. The resulting residue was subjected to silica gel column chromatography (eluent:ethyl acetate/n-hexane =1/3), and then treated with ethyl ether solution saturate d with hydrochloric acid to afford 75 mg (54.5%) of the titled compound.

NMR(CDCl$_3$): δ 1.5 (d, 3 H), 2.1 (s, 3 H), 2.3 (s, 3 H), 2.7 (d, 1 H), 3.1 (m, 1 H), 3.5 (m, 1 H), 4.2 (m, 1 H), 5.3 (q, 1 H), 6.7–7.2 (m, 5 H), 7.4 (m, 2 H), 10.2 (s, 1 H), 14.0 (bs, 1 H).

Example 4–13

The same procedures as in Step 2 of Example 3 above were repeated using 5,6-dimethyl-2-chloro -4-(1-methyl-7-fluoro-1,2,3,4-tetrahydroisoquinolin-2-yl)pyrimidine (0.1 g, 0.33 mmol) and the corresponding aniline derivatives (0.84 mmol) to afford the following titled compounds.

Example 4: Preparation of 5,6-dimethyl-2-phenylamino-4-(1-methyl-7-fluoro-1,2,3,4-tetrahydroisoquinolin-2-yl)pyrimidine hydrochloride NMR(CDCl$_3$): δ 1.6 (d, 3 H), 2.2 (s, 3 H), 2.5 (s, 3 H), 2.9 (m, 1 H) 3.1 (m, 1 H), 3.6 (m, 1 H), 4.3 (m, 1 H), 5.4 (q, 1 H), 6.7–7.0 (m, 2 H), 7.0–7.5 (m, 4 H), 7.6(d, 2 H), 10.2 (s, 1 H), 14.1 (bs, 1 H).

Example 5: Preparation of 5,6-dimethyl-2-(2-methylphenylamino)-4-(1-methyl-7-fluoro-1,2,3,4-tetrahydroisoquinolin-2-yl)pyrimidine hydrochloride NMR(CDCl$_3$): δ 1.6 (d, 3 H), 2.3 (s, 3 H), 2.4 (s, 3 H), 2.5 (d, 3 H), 2.8 (m, 1 H) 3.1 (m, 1 H), 3.6 (m, 1 H), 4.2 (m, 1 H), 5.3 (q, 1 H), 6.7–7.0 (m, 2 H), 7.0–7.4 (m, 3 H), 7.6 (m, 1 H), 9.5 (s, 1 H), 14.4 (bs, 1 H).

Example 6: Preparation of 5,6-dimethyl-2-(2-methyl-4-fluorophenylamino)-4-(1-methyl-7-fluoro-1,2,3,4-tetrahydroisoquinolin-2-yl)pyrimidine hydrochloride NMR(CDCl$_3$): δ 1.5 (d, 3 H), 2.2 (s, 3 H), 2.4 (s, 3 H), 2.5 (s, 3 H), 2.8 (m, 1 H) 3.0 (m, 1 H), 3.5 (m, 1 H), 4.2 (m, 1 H), 5.2 (q, 1 H), 6.7 (d, 1 H), 6.8–7.0 (m, 3 H), 7.1 (m, 1 H), 7.5 (m, 1 H), 9.5 (s, 1 H), 14.3 (bs, 1 H).

Example 7: Preparation of 5,6-dimethyl-2-(3,4-difluorophenylamino)-4-(1-methyl-7-fluoro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.2 (m, 1 H), 3.6 (m, 1 H), 4.3 (m, 1 H), 5.4 (q, 1 H), 6.7–7.0 (m, 2 H), 7.1 (m, 3 H), 7.7 (m, 1 H), 10.5 (s, 1 H), 14.1 (bs, 1 H).

Example 8: Preparation of 5,6-dimethyl-2-(2,4-difluorophenylamino)-4-(1-methyl-7-fluoro-1,2,3,4-tetrahydroisoquinolin-2-yl)pyrimidine hydrochloride NMR(CDCl$_3$): δ 1.5 (d, 3 H), 2.2 (s, 3 H), 2.5 (s, 3 H) 2.8 (m, 1 H) 3.1 (m, 1 H), 3.5 (m, 1 H), 4.2 (m, 1 H), 5.2 (q, 1 H), 6.7 (m, 2 H), 6.9 (m, 2 H), 7.1 (m, 1 H), 7.6 ( t, 1 H), 10.2 (s, 1 H), 14.1 (bs, 1 H).

Example 9: Preparation of 5,6-dimethyl-2-(4-chlorophenylamino)-4-(1-methyl-7-fluoro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.1 (m, 1 H), 3.6 (m, 1 H), 4.3 (m, 1 H), 5.4 (q, 1 H), 6.7–7.0 (m, 2 H), 7.1 (m, 1 H), 7.3 (t, 2 H), 7.5 (d, 2 H), 10.4(s, 1 H), 14.1 (bs, 1 H).

Example 10: Preparation of 5,6-dimethyl-2-(3,4-dichlorophenylamino)-4-(1-methyl-7-fluoro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.2 (m 1 H), 3.6 (m, 1 H), 4.3 (m, 1 H), 5.5 (q, 1 H), 6.7–7.0 (m, 2 H), 7.2 (m, 1 H), 7.3 (t, 2 H), 7.4 (d, 1 H), 8.2 (s, 1 H), 10.6(s, 1 H), 14.1(s, 1 H).

Example 11: Preparation of 5,6-dimethyl-2-(2-fluorophenylamino)-4-(1-methyl-7-fluoro-1,2,3,4-tetrahydroisoquinolin-2-yl)pyrimidine hydrochloride NMR(CDCl$_3$): δ 1.5 (d, 3 H), 2.2 (s, 3 H), 2.5 (s, 3 H), 2.8 (m, 1 H) 3.1 (m. 1 H), 3.5 (m, 1 H), 4.2 (m, 1 H), 5.3 (q, 1 H), 6.7 (d, 1 H), 6.9 (m, 1 H), 7.0–7.4 (m, 4 H), 7.7 (t, 1 H), 9.8 (s, 1 H), 14.6 (s, 1 H).

Example 12: Preparation of 5,6-dimethyl-2-(3-fluorophenylamino)4-(1-methyl-7-fluoro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.2 (m, 1 H), 3.6 (m, 1 H), 4.3) (m, 1 H), 5.4 (q, 1 H), 7.9 (m, 3 H), 7.1–7.4 (m, 3 H), 7.6 (d, 1 H), 10.5 (s, 1 H), 14.2(bs, 1 H).

Example 13: Preparation of 5,6-dimethyl-2-(3-chlorophenylamino)-4-(1-methyl-7-fluoro 1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.2 (m, 1 H), 3.6 (m, 1 H), 4.3 (m, 1 H), 5.5 (q, 1 H), 6.8–7.4 (m, 6H), 8.0(s, 1H), 10.5(s, 1 H), 14.1(bs, 1 H).

Example 14: Preparation of 5,6-dimethyl-2-(4-fluorophenylamino)-4-(1-methyl-6-1,2,3,4-tetrahydroisoquinolin-2-yl)pyrimidine hydrochloride Step 1: 5,6-dimethyl-2-chloro-4-(1-methyl-6-fluoro-1,2,3,4-tetrahydroisoquinolin-2-yl)pyrimidine The same procedures as in Step 1 of Example 3 above were repeated using the compound (3.2 g, 19.4 mmol) prepared in Preparation 3, 5,6-dimethyl-2,4-dichloropyrimidine (3.42 g, 19.4 mmol), and triethylamine (3.24 ml) to afford 2.6 g (43.8%) of the titled compound.

Step 2: 5,6-dimethyl-2-(4-fluorophenylamino)-4-(1-methyl-6-fluoro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-6-fluoro-1,2,3,4-tetrahydroisoquinolin-2-yl)pyrimidine (0.1 g, 0.33 mmol), dimethylformamide (5 ml), and 4-fluoroaniline (0.08 ml, 0.84 mmol) to afford 84 mg (61%) of the titled compound.

NMR(CDCl$_3$): δ 1.5 (d, 3 H), 2.1 (s, 3 H), 2.4 (s, 3 H), 3.1 (m, 1 H), 3.5 (m, 1 H), 4.2 (m, 1H), 5.3 (q, 1 H), 6.7–7.2 (m, 5 H), 7.5 (m 2 H), 10.2 (s, 1 H), 14.1 (bs, 1 H).

Example 15–23

The same procedures as in Step 2 of Example 3 above were repeated using 5,6-dimethyl-2-chloro-4-(1 -methyl-6- fluoro-1,2,3,4-tetrahydroisoquinolin-2-yl)pyrimidine (0.1 g 0.33 mmol) prepared in Step 1 of Example 14 and the corresponding aniline derivatives (0.84 mmol) to afford the following titled compounds.

Example 15: Preparation of 5,6-dimethyl-2-phenylamino-4-(1-methyl-6-fluoro-1,2,3,4-tetrahydroisoquinolin-2-yl)pyrimidine hydrochloride NMR(CDCl$_3$): δ 1.6 (d, 3 H), 2.2 (s, 3 H), 2.5 (s, 3 H), 2.8 (m, 3 H), 3.2 (m, 1 H), 3.6 (m, 1 H), 4.3 ( m, 1 H), 5.4 (q, 1 H), 6.8–7.6 (m, 8 H), 10.2 (s, 1 H).

Example 16: Preparation of 5,6-dimethyl-2-(2-methylphenylamino)4-(1-methyl-6-fluoro-1,2,3,4-tetrahydroisoquinolin-2-yl)pyrimidine hydrochloride NMR(CDCl$_3$): δ 1.6 (d, 3 H), 2.2 (s, 3 H), 2.4 (s, 3 H), 2.5 (s, 3 H) 2.8 (m, 1 H), 3.1 (m, 1 H), 3.5 (m, 1 H), 4.2 (m, 1 H), 5.3 (q, 1 H), 6.8–7.1 (m, 3 H), 7.2 (m, 3 H), 7.6 (d, 1 H), 9.5 (s, 1 H), 14.4(bs, 1 H).

Example 17: Preparation of 5,6-dimethyl-2-(2-methyl-4-fluorophenylamino)-4-(1-methyl-6-fluoro-1,2,3,4-tetrahydroisoquinolin-2-yl)pyrimidine hydrochloride NMR(CDCl$_3$): δ 1.5 (d, 3 H), 2.2 (s, 3 H), 2.4 (s, 3 H), 2.5 (s, 3 H), 2.8 (m, 1 H) 3.1 (m, 1 H), 3.5 (m, 1 H), 4.2 (m, 1 H), 5.2 (q, 1 H), 6.8–7.1 (m, 5 H), 7.5 (m, 1 H), 9.6 (s, 1 H), 14.4 (bs, 1 H).

Example 18: Preparation of 5,6-dimethyl-2-(3,4-difluorophenylamino)4-(1-methyl-6-fluoro- 1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H) 3.2 (m, 1 H), 3.6 (m, 1 H), 4.3 (m, 1 H), 5.4 (q, 1 H), 6.8–7.3 (m, 5 H), 7.8 (m, 1 H), 10.5 (s. 1 H).

Example 19: Preparation of 5,6-dimethyl-2-(2,4-difluorophenylamino)-4-(1-methyl-6-fluoro-1,2,3,4,-tetrahydroisoquinolin-2-yl)pyrimidine hydrochloride NMR(CDCl$_3$): δ 1.5 (d, 3 H), 2.2 (s, 3 H), 2.5 (s, 3 H), 2.8 (m, 1 H) 3.1 (m, 1 H), 3.5 (m, 1 H), 4.2 (m, 1 H), 5.2 (q, 1 H), 6.7–7.0 (m, 5 H), 7.6 (m, 1 H), 9.5(s, 1 H).

Example 20: Preparation of 5,6-dimethyl-2-(4-chlorophenylamino)4-(1-methyl-6-fluoro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (m, 1 H), 3.2 (m, 1 H), 3.6 (m, 1 H), 4.3 (m, 1 H), 5.4 (q, 1 H), 6.8–7.2 (m, 4 H), 7.3 (t, 2 H), 7.5 (d, 1 H), 10.4 (s, 1 H), 14.1 (bs, 1 H).

Example 21: Preparation of 5,6-dimethyl-2-(2-fluorophenylamino)-4-(1-methyl-6-fluoro-1,2,3,4-tetrahydroisoquinolin-2-yl)pyrimidine hydrochloride NMR(CDCl$_3$): δ 1.5 (d, 3 H), 2.2 (s, 3 H), 2.5 (s, 3 H), 2.8 (m, 1 H) 3.2 (m, 1 H), 3.6 (m, 1 H), 4.2 (m, 1 H), 5.3 (q, 1 H), 6.7–7.1 (m, 4 H), 7.2 (m, 2 H), 7.8 (m, 1 H), 9.4 (s, 1 H).

Example 22: Preparation of 5,6-dimethyl-2-(3-fluorophenylamino)-4-(1-methyl-6-fluoro- 1,2,3,4-tetrahydroisoquinolin-2-yl)pyrimidine hydrochloride NMR(CDCl$_3$): δ 1.7 (d, 3 H), 2.3 (s, 3 H), 2.5 (s, 3 H), 2.9 (m, 1 H), 3.2 (m, 1 H), 3.6 (m, 1 H), 4.3 (m, 1 H), 5.5 (q, 1 H), 6.8–7.0 (m, 3 H), 7.1–7.4 (m, 3 H), 7.7 (d, 1 H), 10.5 (s, 1 H), 14.1 (bs, 1 H).

Example 23: Preparation of 5,6-dimethyl-2-(3-chlorophenylamino)-4-(1-methyl-6-fluoro-1,2,3,4-tetrahydroisoquinolin-2-yl)pyrimidine hydrochloride NMR(CDCl$_3$): δ 1.7 (d, 3 H), 2.3 (s, 3 H), 2.5 (s, 3 H), 3.0 (m, 1 H), 3.3 (m, 1 H), 3.7 (m, 1 H), 4.3 (m, 1 H), 5.5 (q, 1 H), 6.8–7.1 (m, 3 H), 7.1–7.4 (m, 3 H), 8.1 (s, 1 H), 10.5 (s, 1 H), 14.1 (bs, 1 H).

Example 24: Preparation of 5-methyl-6-fluoromethyl-2-(4-fluorophenylamino)-4-(1-methyl-1,2,3,4-tetrahydroisoquinolin-2-yl)-pyrimidine hydrochloride The solution of 6-hydroxymethyl-5-methyl-2-(4-fluorophenyl-amino)4-(1-methyl-1,2,3,4-tetrahydroisoquinolin-2-yl)pyrimidine (0.19 g, 0.5 mmol) prepared in accordance with WO 98/43968 in dichloromethane (5 ml) and cooled to –75° C. and (diethylamino) sulfur trifluoride (0.15 ml, 2.26mmol) was dropwise added thereto. The reaction mixture was stirred for 2 hours at –75° C., further stirred for 2 hours at –45 ° C., and slowly heated to room temperature. The reaction mixture was stirred for 18 hours at room temperature, and then water was added thereto to terminate the reaction. The extracted organic layer was dried over anhydrous sodium sulfate and concentrated in vacuo. The resulting residue was subjected to silica gel column column chromatography (eluent:ethyl acetate/hexane=⅓), and then treated with ethyl ether solution saturated with hydrochloric acid to afford 72 mg (34.5%) of the titled compound.

NMR (DMSO-d$_6$): δ 1.6 (d, 3 H), 2.2(s, 3 H), 2.8(m, 1 H), 3.1(m, 1 H), 3.5(m, 1 H), 4.2(m, 1 H), 5.3(q, 1 H), 5.5(d, 2 H), 7.2(m, 6 H), 7.6(m, 2 H), 10.0(br, 1 H).

Example 25: Preparation of 5-fluoromethyl-6-methyl-2-(4-fluorophenylamino)-4-(1-methyl-1,2,3,4-tetrahydroisoquinolin-2-yl)-pyrimidine hydrochloride The same procedures as in Example 24 above were repeated using 5-hydroxymethyl-6-methyl-2-(4-fluorophenylamino)-4-(1-methyl-1,2,3,4-tetrahydroisoquinolin-2-yl)pyrimidine (0.19 g, 0.5mmol) prepared in accordance with WO 98/43968, dichloromethane (5 ml), and (diethylamino)sulfur trifluoride (0.15 ml, 2.26 mmol) to afford 27 mg (14%) of the titled compound.

NMR(CDCl$_3$): δ 1.6(d, 3 H), 2.2(s, 3 H), 2.7(m, 1 H), 3.1(m, 1 H), 3.5(m, 1 H), 4.0(m, 1 H), 5.1(m, 2 H), 5.4(s, 1 H), 6.9(m, 3 H), 7.1(m, 4 H), 7.5(m, 2 H).

Example 26: Preparation of 5,6-dimethyl-2-(4-fluorophenylamino)-4-(1-fluoromethyl-1,2,3,4-tetrahydroisoquinolin-2-yl)pyrimidine hydrochloride The same procedures as in Example 24 above were repeated using 5,6-methyl-2-(4-fluorophenylamino)-4-(1-hydroxymethyl-1,2,3,4-tetrahydroisoquinolin-2-yl)pyrimidine(0.1 g, 0.26 mmol) prepared in accordance with WO 98/43968, dichloromethane (5 ml), and (diethylamino) sulfur trifluoride (77 µl, 0.58 mmol) to afford 0.1 g (92.2 %) of the titled compound.

NMR (DMSO-d$_6$): δ 2.2 (d, 6 H), 3.0 (m, 1 H), 3.9 (m, 1 H), 4.4 (m, 2 H). 5.0 (m, 1 H), 5,6 (m, 1 H), 7.2 (m, 6 H), 7.6 (m, 2 H).

Example 27: Preparation of 5,6-dimethyl-2-(4-fluorophenylamino)-4-(1-methyl-5-fluoro-1,2,3,4-tetrahydroisoquinolin-2-yl)pyrimidine hydrochloride Step 1: 5,6-dimethyl-2-chloro-4-(1-methyl-5-fluoro-1,2,3,4-tetrahydroisoquinolin-2-yl)pyrimidine The same procedures as in Step 1 of Example 3 above were repeated using the compound (1.2 g, 7.3 mmol) prepared in Preparation 4, dimethylformamide (10 ml), 5,6- dimethyl-2,4-dichloropyrimidine (1.3 g, 7.3 mmol), and triethylamine (1.22 ml) to afford 0.94 g (42%) of the titled compound.

Step 2: 5,6-dimethyl-2-(4-fluorophenylamino)-4(1-methyl-5-fluoro-1,2,3,4-tetrahydroisoquinolin-2-yl)pyrimidine hydrochloride The same procedures as in Step 2 of Example 3 above were repeated using 5,6-dimethyl-2-chloro-(1-methyl-5-fluoro-1,2,3,4-tetrahydroisoquinolin-2-yl)pyrimidine (0.1 g, 0.33 mmol) prepared in Step 1 above, dimethylformamide (5 ml), and 4-fluoroaniline (0.08 ml, 0.84 mmol) to afford 75 mg (54.5 %) of the titled compound.

NMR(CDCl$_3$): δ 1.6 (d, 3 H), 2.2 (s, 3 H), 2.5 (s, 3 H), 3.1 (m, 1 H), 3.6 (m, 1 H), 4.3 (m, 1 H), 5.4 (q, 1 H), 6.9–7.4 (m, 5 H), 7.5 (m, 2 H), 10.2 (s, 1 H), 14.1 (bs, 1 H).

Example 28: Preparation of 5,6-dimethyl-2-phenylamino-4-(1-methyl-5-fluoro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-5-fluoro-1,2,3,4-tetrahydroisoquinolin-2-yl)pyrimidine (0.1 g, 0.33 mmol) prepared in Step 1 of Example 27 and aniline (0.84 mmol) to afford 82 mg (59.6%) of the titled compound.

NMR(CDCl$_3$): δ 1.6 (d, 3 H), 2.2 (s, 3 H), 2.5 (s, 3 H), 3.2 (m, 1 H), 3.5 (m, 1 H), 4.3 (m, 1 H), 5.4 (q, 1 H), 6.8–7.2 (m, 6 H), 7.51 (m, 2 H), 10.2 (s, 1 H), 14.1 (bs, 1 H).

Example 29: Preparation of 5,6-dimethyl-2-(4-fluorophenylamino)-4-(1-methyl-7-chloro-1,2,3,4-tetrahydroisoquinolin-2-yl)pyrimidine hydrochloride Step 1: 5,6-dimethyl-2-chloro-4-(1-methyl-7-chloro-1 2,3,4-tetrahydroisoquinolin-2-yl)pyrimidine The same procedures as in Step 1 of Example 3 above were repeated using the compound (1.5 g, 8.26 mmol) prepared in Preparation 5, dimethylformamide (10 ml), 5,6-dimethyl-2,4-dichloropyrimidine (1.46 g, 8.26 mmol), and triethylamine(1.38 ml) to afford 1.12 g (41%) of the titled compound.

Step 2: 5,6-dimethyl-2-(4-fluorophenylamino)-4-(1-methyl-7-chloro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-7-chloro-1,2,3,4-tetrahydroisoquinolin-2-yl)pyrimidine (0.1 g, 0.31 mmol) prepared in Step 1 above, dimethylformamide (5 ml), and 4-fluoroaniline (0.07 ml, 0.74mmol) to afford 82 mg (61.3%) of the titled compound NMR(CDCl$_3$): δ 1.6 (d, 3 H), 2.2 (s, 3 H), 2.4 (s, 3 H), 2.8 (d, 1 H), 3.1 (m, 1 H), 3.6 (m, 1 H), 4.2 (m, 1 H), 5.3 (q, 1 H), 6.9–7.2 (m, 5 H), 7.5 (m, 2 H), 10.2 (s, 1 H), 14.1 (bs,. 1 H)

Example 30–32

The same procedures as in Step 2 of Example 3 above were repeated using 5 6-dimethyl-2-chloro-4-(1-methyl-7-chloro-1,2,3,4-tetrahydroisoquinolin-2-yl)pyrimidine (0.1 g, 0.31 mmol) prepared in Step 1 of Example 29 and the corresponding aniline derivatives (0.74 mmol) to afford following, titled compounds.

Example 30: Preparation of 5,6-dimethyl-2-phenylamino-4-(1-methyl-7-chloro-1,2,3,4,-tetrahydroisoquinolin-2-yl)pyrimidine hydrochloride NMR(CDCl$_3$): δ 1.6 (d, 3 H), 2.2 (s, 3 H), 2.5 (s, 3 H), 2.9 (d, 1 H), 3.2 (m, 1 H), 3.6 (m, 1 H), 4.3 (m, 1 H), 5.4 (q, 1 H), 7.0–7.5 (m, 6 H), 7.6 (m, 2 H), 10.2 (s, 1 H), 14.1 (bs, 1 H).

Example 31: Preparation of 5,6-dimethyl-2-(2-methylphenylamino)-4-(1-methyl-7-chloro-1,2,3,4-tetrahydroisoquinolin-2-yl)pyrimidine hydrochloride NMR(CDCl$_3$): δ 1.5 (d, 3 H), 2.2 (s, 3 H), 2.4 (s, 3 H), 2.5 (s, 3 H), 2.8 (d, 1 H), 3.0 (m, 1 H), 3.5 (m, 1 H), 4.2 (m, 1 H), 5.2 (q, 1 H), 6.9–7.3 (m, 6 H), 7.6 (d, 1 H), 9.5 (s, 1 H), 14.5 (bs, 1 H).

Example 32: Preparation of 5,6-dimethyl-2-(3,4-difluorophenylamino)-4-(1 -methyl-7-chloro -1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 2.9 (d, 1 H), 3.2 (m, 1 H), 3.6 (m, 1 H), 4.3 (m, 1 H), 5.4 (q, 1 H), 7.0–7.4 (m, 5 H), 7.7 (m, 1 H), 10.5 (s, 1 H), 14.1 (bs, 1 Hl).

Example 33: Preparation of 5,6-dimethyl-2-(4-fluorophenylamino)-4-(1-methyl-6-chloro-1,2,3,4-tetrahydroisoquinolin-2-yl)pyrimidine hydrochloride Step 1: 5,6-dimethyl-2-chloro-4-(1-methyl-6-chloro- 1,2,3,4-tetrahydroisoquinolin-2-yl)pyrimidine The same procedures as in Step 1 of Example 3 above were repeated using the compound (4.5 g, 24.77 mmol) prepared in Preparation 6, dimethylformamide (15 ml), 5,6-dimethyl-2,4-dichloropyrimidine (4.39 g, 24.77 mmol), and triethylamine (4.14 ml) to afford 3.43 g (43%) of the titled compound.

Step 2: 5,6-dimethyl-2-(4-fluorophenylamino)-4-(1-methyl-6-chloro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-6-chloro- 1,2,3,4-tetrahydroisoquinolin-2-yl)pyrimidine (0.1 g, 0.31 mmol) prepared in Step 1 above, dimethylformamide (5 ml), and 4-fluoroaniline (0.07 ml, 0.74 mmol) to afford 7 mg (53%) of the titled compound.

NMR(CDCl$_3$): δ 1.6 (d, 3 H), 2.2 (s, 3 H), 2.5 (s, 3 H), 2.9 (m, 1 H), 3.2 (m, 1 H), 3.6 (m, 1 H), 4.3 (m, 1 H), 5.4 (q, 1 H), 6.9–7.3 (m, 4 H), 7.5 (m, 2 H), 10.2 (s, 1 H), 14.1 (bs, 1 H).

Example 34: Preparation of 5,6-dimethyl-2-phenylamino-4-(1-methyl-6-chloro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-6-chloro-1,2,3,4-tetrahydroisoquinolin-2-yl)pyrimidine (0.1 g, 0.31 mmol) prepared in Step 1 of Example 33 and aniline (0.74 mmol) to afford 73 mg (54.3%) of the titled compound NMR(CDCl$_3$): δ 1.6 (d, 3 H), 2.2 (s, 3 H), 2.5 (s, 3 H), 2.9 (m, 1 H), 3.2 (m, 1 H), 3.6 (m, 1 H), 4.3 (m, 1 H), 5.4 (q, 1 H), 7.1 (d, 1 H), 7.2 (m, 3 H), 7.4 (m, 2 H), 7.6 (d, 2 H), 10.2 (s, 1 H), 14.1 (bs, 1 H).

Example 35: Preparation of 5,6-dimethyl-2-(4-fluorophenylamino)-4-(1-methyl-5-chloro- 1,2,3,4-tetrahydroisoquinolin-2-yl)pyrimidine hydrochloride Step 1: 5,6-dimethyl-2-chloro-4-(1-methyl-5-chloro-1,2,3,4-tetrahydroisoquinolin-2-yl)pyrimidine The same procedures as in Step 1 of Example 3 were repeated using the compound (4.5 g, 24.77 mmol) prepared in Preparation 7, dimethylformamide (15 ml), 5,6-dimethyl-2,4-dichloropyrimidine (4.39 g, 24.77 mmol), and triethylamine (4.14 ml) to afford 3.21 g (40.2%) of the titled compound.

Step 2: 5,6-dimethyl-2-(4-fluorophenylamino)-4-(1-methyl-5-chloro-1,2,3,4-tetrahydroisoquinolin-2-yl)pyrimidine hydrochloride The same procedures as in Step 2 of Example 3 above were repeated using 5,6-dimethyl-2-chloro-4-(1-methyl-5-chloro- 1,2,3,4-tetrahydroisoquinolin-2-yl)pyrimidine (0.1 g, 0.31 mmol) prepared in Step 1 above, dimethylformamide (5 ml), and 4-fluoroaniline (0.07 ml, 0.74 mmol) to afford 67 mg (50%) of the titled compound.

NMR(CDCl$_3$): δ 1.6 (d, 3 H), 2.2 (s, 3 H), 2.5 (s, 3 H), 3.1 (m, 1 H), 3.6 (m, 1 H), 4.3 (m, 1 H), 5.4 (q, 1 H), 6.9–7.4 (m, 5 H), 7.5(m, 2 H), 10.2 (s, 1 H).

Examples 36–44

The same procedures as in Step 2 of Example 3 above were repeated using 5,6dimethyl-2-chloro-4-(1-methyl-5-chloro-1,2,3,4-tetrahydroisoquinolin-2-yl)pyrimidine (0.1 g, 0.31 mmol) prepared in Step 1 of Example 35 and the corresponding aniline derivatives (0.74 mmol) to afford the following the titled compound.

Example 36: Preparation of 5,6-dimethyl-2-phenylamino-4-(1-methyl-5-chloro-1,2,3,4-tetrahydroisoquinolin-2-yl)pyrimidine hydrochloride NMR(CDCl$_3$): δ 1.6 (d, 3 H), 2.2 (s, 3 H), 2.4 (s. 3 H), 3.1 (m, 1 H), 3.5 (m, 1 H), 4.3 (m, 1 H) 5.3 (q, 1 H), 6.8–7.2 (m, 6 H), 7.5 (m, 2 H), 10.2 (s, 1 H), 14.1 (bs. Hl).

Example 37: Preparation of 5,6-dimethyl-2-(2-methylphenylamino)-4-(1-methyl-5-chloro-1,2,3,4-tetrahydroisoquinolin-2-yl)pyrimidine hydrochloride NMR(CDCl$_3$): δ 1.6 (d, 3 H), 2.2 (s, 3 H), 2.4 (s, 3 H), 2.5 (s, 3 H), 3.0 (m, 2 H), 3.5 (m, 1 H), 4.3 (m, 1 H), 5.3 (q, 1 H), 6.9 (d, 1 H), 7.0–7.4 (m, 5 H), 7.6 (d, 1 H), 9.6 (s, 1 H).

Example 38: Preparation of 5,6-dimethyl-2-(3,4-difluorophenylamino)-4-(1-methyl-5-chloro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 31 H), 3.1 (m, 2 H), 3.6 (m, 1 H), 4.4 (m, 1 H), 5.5 (q, 1 H), 7.0–7.4 (m, 5 H), 7.7 (m, 1 H), 10.5 (s, 1 H), 14.1 (bs, 1 H).

Example 39: Preparation of 5,6-dimethyl-2-(2,4-difluorophenylamino)-4-(1-methyl-5-chloro-1,2,3,4-tetrahydroisoquinolin-2-yl)pyrimidine hydrochloride NMR(CDCl$_3$): δ 1.6 (d, 3 H), 2.2 (s, 3 H), 2.5 (s, 3 H), 3.0 (m, 2 H), 3.5 (m, 1 H), 4.2 (m, 1 H), 5.3 (q, 1 H), 6.8–7.1 (m, 3 H), 7.1–7.4 (m,2 H), 7.6 (m, 1 H), 9.7 (s, 1 H), 14.5 (bs, 1 H)

Example 40: Preparation of 5,6-dimethyl-2-(4-chlorophenylamino)-4-(1-methyl-5-chloro-1,2,3,4-tetrahydroisoquinolin-2-yl)pyrimidine hydrochloride NMR(CDCl$_3$): δ 1.7 (d, 3 H), 2.2 (s, 3 H), 2.5 (s, 3 H), 3.1 (m, 2 H), 3.6 (m, 1 H), 4.3 (m, 1 H), 5.4 (q, 1 H), 7.1 (d, 1 H), 7.1–7.4 (m, 5 H), 7.6 (d, 1 H), 10.4 (s, 1 H), 14.1(bs, 1 H).

Example 41: Preparation of 5,6-dimethyl-2-(3,4-dichlorophenylamino)-4-(1-methyl-5-chloro-1,2,3,4-tetrahydroisoquinolin-2-yl)pyrimidine hydrochloride NMR(CDCl$_3$): δ 1.7 (d, 3 H), 2.3 (s, 3 H), 2.5 (s, 3 H), 3.1 (m, 2 H), 3.7 (m, 1 H), 4.4 (m, 1 H), 5.6 (q, 1 H), 7.0 (d, 1 H), 7.0–7.5 (m, 5 H), 8.2 (s, 1 H), 10.7 (s, 1 H), 14.1 (bs, 1 H).

Example 42: Preparation of 5,6-dimethyl-2-(2-fluorophenylamino)-4-(1-methyl-5-chloro- 1,2,3,4-tetrahydroisoquinolin-2-yl)pyrimidine hydrochloride NMR(CDCl$_3$): δ 1.6 (d, 3 H). 2.3 (s, 3 H), 2.6 (s, 3 H), 3.0 (m, 2 H), 3.6 (m, 1 H), 4.3 (m, 1 H), 5.4 (q, 1 H), 7.0 (d, 1 H) 7.1–7.4 (m, 5H), 7.7 (t, 1 H), 9.8 (s, 1 H), 14.6(bs, 1 H).

Example 43: Preparation of 5,6-dimethyl-2-(3-fluorophenylamino)-4-(1-methyl-5-chloro- 1,2,3,4-tetrahydroisoquinolin-2-yl)pyrimidine hydrochloride NMR(CDCl$_3$): δ 1.7 (d, 3 H), 2.3 (s, 3 H), 2.5 (s, 3 H), 3.1 (m, 2 H), 3.6 (m, 1 H), 4.4 (m, 1 H), 5.5 (q, 1 H), 6.9 (t, 11 H), 7.1 (d, 1 H), 7.2–7.4 (m, 4 H), 7.7 (d, 1 H), 10.5 (s, 1 H), 14.1(bs, 1 H).

Example 44: Preparation of 5,6-dimethyl-2-(3-chlorophenylamino)-4-(1-methyl-5-chloro-1,2,3,4-tetrahydroisoquinolin-2-yl)pyrimidine hydrochloride NMR(CDCl$_3$): δ 1.7 (d, 3 H), 2.3 (s, 3 H), 2.5 (s, 3 H), 3.1 (m, 2 H), 3.7(m, 1 H), 4.4 (m, 1 H), 5.6 (q, 1 H), 7.0–7.4 (m, 6 H), 8.1 (s, 1 H), 10.5(s, 1 H), 14.1 (bs, 1 H).

Test Example 1: Inhibition of proton pump (H$^+$/K$^+$-ATPase) activity

The gastric vesicle as an enzyme source was prepared by the same method as in the Experiment 1—1 of WO 94/14795. Further, the inhibitory effect of proton pump activity was measured by the same method as in Experiment 1–2 of WO 94/14795.

Namely, the proton pump activity stimulated by Mg$^{++}$ was used as a negative control group, and the activity stimulated by Mg$^{++}$ and K$^+$ was used as a positive control group. Omeprazole was used as the control compound.

Test tubes were divided into 4 groups: Group 1 as negative control group (n=3), Group 2 as positive control group (n=3), Group 3 (n=5×2) to be administered with the compound of the present invention and Group 4 (n=5×2) to be administered with the control compound.

The inhibitory effects of Group 3 and 4 on proton pump activity were measured by employing the compounds prepared in Examples and omeprazole, respectively, each of which was dissolved in dimethyl sulfoxide (DMSO) at 5 different concentrations.

To each of Groups 1, 2, 3, and 4 was added 0.1 ml of magnesium chloride (4 mM) dissolved in 40 mM Tris-HCl buffer (pH 6.4) and 100 μg of enzyme source. The 50 μl of potassium chloride (60 mM) and 50 μl of ammonium chloride (6 mM) dissolved in 40 mM Tris-HCl buffer (pH 6.4) were added to all groups except for Group 1.

10 μl of dimethyl sulfoxide was added to each of Group 1 and 2; and to Group 3 was added 1 μl of dimethyl sulfoxide solution prepared by dissolving compound of Example at 5 different concentrations (n=5×2). To Group 4, was added 10 μl of the solution prepared by dissolving omeprazole in dimethyl sulfoxide at 5 different concentrations (40, 20, 10, 5, 2.5 μM) (n=5×2). 4 mM Tris-HCl buffer (pH 6.4) was added thereto so as to make the total volume 400 μl.

Thereafter the test tubes of each Group were placed at 37° C. for 30 minutes for the preincubation. ATP solution (6.6 mM) was added until the total volume became 500 μl. After the reaction was carried out at 37° C. for 30 minutes, 25% cold trichloroactic acid was added to terminate the enzyme reaction. The released inorganic phosphorous was measured by an automatic analyzer (Express 550, Corning).

The difference between Group 1 and Group 2 represents the proton pump activity activated by K$^+$ only. The IC$_{50}$s of Group 3 and 4 were calculated using the Linear Regression method. The concentrations of the test compounds inhibiting 50% of the proton pump activity are represented as IC$_{50}$ in Table 1.

TABLE 1

Inhibitory effects on proton pump (H$^+$/K$^+$-ATPase) activity

| Compound | IC$_{50}$ ($\mu$M) |
|---|---|
| Example 1 | 1.6 |
| Example 2 | 3.8 |
| Example 4 | 1.0 |
| Example 5 | 0.6 |
| Example 6 | 0.3 |
| Example 7 | 2.6 |
| Example 8 | 0.7 |
| Example 9 | 0.9 |
| Example 11 | 1.9 |
| Example 12 | 3.2 |
| Example 14 | 0.7 |
| Example 17 | 0.2 |
| Example 19 | 1.0 |
| Example 20 | 1.2 |
| Example 24 | 0.9 |
| Example 25 | 4.1 |
| Example 26 | 3.7 |
| Example 35 | 0.9 |
| Example 39 | 0.9 |
| Omeprazole | 11.5 |

As shown in Table 1, the compounds of the present invention exhibit the highly potent acid pump inhibitory activity over omeprazole.

Test Example 2: Inhibition of gastric secretion

In accordance with the method disclosed in Shay, H., et al., Gastroenterology 5, 43–61 (1945), the inhibitory activity against acid secretion was evaluated.

Sprague-Dawley rats having a body weight of 200±10 g were divided into 3 groups (n=5) and deprived of food for 24 hours before the experiment with free access to water. Under ether anesthesia, the abdomen was incised, and the pylorus was ligated.

As a comparative group, Group 1 was administered intraduodenally in the volume of 0.5 ml/200 g of 0.5% methylcellulose solution. Group 2 and 3 were administered intraduodenally in the volume of 0.5 ml/200 g of the compound of Example and omeprazole, respectively, each of which was suspended in 0.5% methylcellulose solution at a concentration of 10 mg/kg. After 5 hours from ligation, the rats were sacrificed, and the gastric contents were collected.

The gastric juice collected was centrifuged at 1,000 g to remove precipitates. The volume and pH of the gastric juice were measured. Relative volumes, relative acid concentrations, and relative acid outputs of the test compounds were calculated from equations (I), (II), and (III) and the results are shown in Table 2.

Relative volume ------------------------------ ---------------(I) =(the average volume of gastric juice of Group 1 - the average volume of gastric juice of Group 2) /(the average volume of gastric juice of Group 1 - the average volume of gastric juice of Group 3)

Relative acid concentration -------- -----------------------(II) =(the average acidity of Group 1 - the average acidity of Group 2) /(the average acidity of Group 1 - the average acidity of Group 3)

Relative acid output ------------------------------------- (III) =(the total volume of acid output of Group 1 - the total volume of acid output of Group 2) /(the total volume of acid output of Group 1 - the total volume of acid output of Group 3)

TABLE 2

| Compound | Relative volume | Relative conc. | Relative acid output |
|---|---|---|---|
| Example 1 | 0.6 | 0.7 | 0.8 |
| Example 2 | 0.9 | 0.7 | 0.9 |
| Example 3 | 0.7 | 1.2 | 0.9 |
| Example 4 | 0.9 | 1.1 | 0.9 |
| Example 6 | 0.7 | 0.8 | 0.8 |
| Example 14 | 1.9 | 1.3 | 1.3 |
| Example 15 | 0.7 | 1.6 | 1.0 |
| Example 16 | 1.0 | 0.9 | 0.9 |
| Example 24 | 0.6 | 1.1 | 1.0 |
| Example 29 | 0.9 | 1.2 | 1.0 |
| Example 37 | 0.9 | 0.8 | 0.9 |

As shown in Table 2, the compounds of the present invention exhibit the highly potent inhibitory activity against gastric acid secretion over omeprazole.

What is claimed is:

1. A pyrimidine derivative of formula (I) or a pharmaceutically acceptable non-toxic salt thereof:

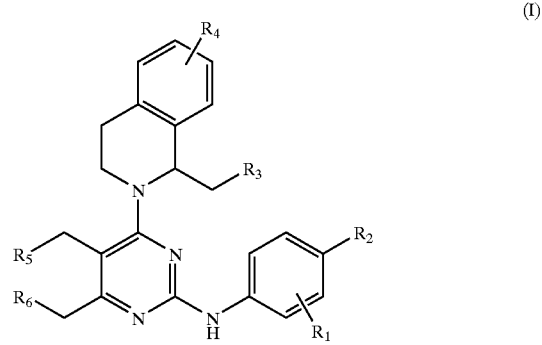

wherein R$_1$ is selected from the group consisting of hydrogen, methyl, and halogen and R$_2$, R$_3$, R$_4$, R$_5$ and R$_6$ are each independently selected from the group consisting of hydrogen and a halogen, provided that when all of R$_3$, R$_4$, R$_5$ and R$_6$ are hydrogen, R$_1$ and R$_2$ are each independently a halogen.

2. The pyrimidine derivative of formula (I) or the pharmaceutically acceptable non-toxic salt thereof according to claim 1, wherein R$_1$, R$_2$, R$_3$, R$_4$, R$_5$ and R$_6$ are each independently a halogen, and the halogen is selected from the group consisting of fluoro and chloro.

3. A pharmaceutical composition comprising a therapeutically effective amount of the pyrimidine derivative or a pharmaceutically acceptable non-toxic salt thereof as defined in claim 1, and a pharmaceutically acceptable carrier or excipient.

4. A pharmaceutically acceptable non-toxic salt of the pyrimidine derivative of formula (I) as recited in claim 1, wherein the salt is an acidic salt.

5. A pharmaceutically acceptable non-toxic salt of the pyrimidine derivative of formula (I) as recited in claim 1, wherein the salt is selected from the group consisting of a hydrochloride, maleate, sulfate, phosphate, mesylate, nitrate, tartrate, fumarate, citrate and acetate salt.

6. The pyrimidine derivative of formula (I) or a pharmaceutically acceptable non-toxic salt thereof as recited in claim 1, wherein the derivative is of formula (I-1):

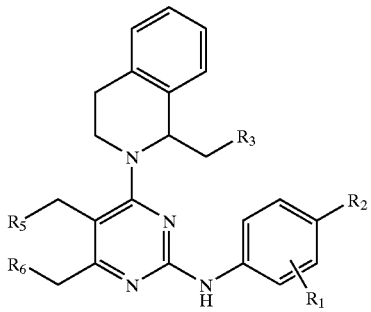

(I-1)

wherein $R_1$ is selected from the group consisting of hydrogen, methyl, and halogen; and $R_2$, $R_3$, $R_5$ and R are each independently selected from the group consisting of hydrogen and a halogen, provided that at least one of $R_3$, $R_5$ and R, is halogen.

7. The pyrimidine derivative of formula (I) or a pharmaceutically acceptable non-toxic salt thereof as recited in claim 1, wherein the derivative is of formula (I-2):

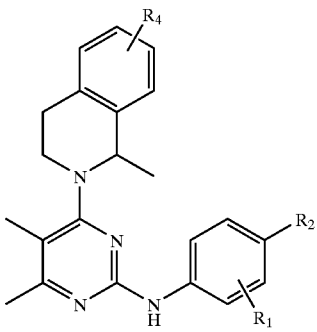

(I-2)

wherein $R_1$ is selected from the group consisting of hydrogen, methyl, and halogen; and $R_2$ and $R_4$ are each independently selected from the group consisting of hydrogen and a halogen, provided that when $R_4$ is hydrogen, $R_1$ and $R_2$ are each independently a halogen.

8. The pharmaceutical composition of claim 3 in a form suitable for oral or intraperitoneal administration.

9. A method of treating a peptic ulcer disease comprising administering to a patient in need of such treatment a pyrimidine derivative or pharmaceutically acceptable non-toxic salt thereof as defined in claim 1 in a therapeutically effective amount.

10. 5,6-Dimethyl-2-(4-fluorophenylamino)-4-(1-methyl-7-fluoro-1,2,3,4-tetrahydroisoquinolin-2-yl)pyrimidine or a pharmaceutically acceptable salt thereof.

11. 5,6-Dimethyl-2-(4-fluorophenylamino)-4-(1-methyl-6-fluoro-1,2,3,4-tetrahydroisoquinolin-2-yl)pyrimidine or a pharmaceutically acceptable salt thereof.

12. 5,6-Dimethyl-2-phenylamino-4-(1-methyl-6-fluoro-1,2,3,4-tetrahydroisoquinolin-2-yl)pyrimidine or a pharmaceutically acceptable salt thereof.

13. 5,6-Dimethyl-2-(4-fluorophenylamino)-4-(1-methyl-7-chloro-1,2,3,4-tetrahydroisoquinolin-2-yl)pyrimidine or a pharmaceutically acceptable salt thereof.

* * * * *